United States Patent [19]  
Frank

[11] 4,430,266  
[45] Feb. 7, 1984

[54] PROCESS FOR PRODUCING AN INSULIN PRECURSOR

[75] Inventor: Bruce H. Frank, Indianapolis, Ind.

[73] Assignee: Eli Lilly and Company, Indianapolis, Ind.

[21] Appl. No.: 349,397

[22] Filed: Feb. 16, 1982

Related U.S. Application Data

[63] Continuation of Ser. No. 210,696, Nov. 28, 1980, abandoned, which is a continuation-in-part of Ser. No. 134,389, Mar. 27, 1980, abandoned.

[51] Int. Cl.³ .................... C07C 103/52; C07G 7/00
[52] U.S. Cl. .................................................. 260/112.7
[58] Field of Search .................................... 260/112.7

[56] References Cited

U.S. PATENT DOCUMENTS 3,847,893 11/1974 Brandenburg et al. .......... 260/112.7

OTHER PUBLICATIONS

Dixon et al.—Nature, vol. 188, (1960), pp. 721–724.
Steiner et al.—Biochemistry, vol. 60, 1968, pp. 623–629.
Diabetes 13, (1964), pp. 339–347.
Biochemistry, vol. 55, 1966, pp. 1455–1461.

Primary Examiner—Frederick E. Waddell
Attorney, Agent, or Firm—William C. Martens, Jr.; Arthur R. Whale

[57] ABSTRACT

A proinsulin-like disulfide insulin precursor is produced from its corresponding linear chain S-sulfonate insulin precursor by reacting the S-sulfonate with a mercaptan in an amount which provides from about 1 to about 5 —SH moieties per —$SO_3^-$ moiety in an aqueous medium at a pH of from about 7 to about 11.5 and at an S-sulfonate concentration of up to about 10 mg. per ml. of aqueous medium.

17 Claims, No Drawings

PROCESS FOR PRODUCING AN INSULIN PRECURSOR

CROSS REFERENCE

This application is a continuation of application Ser. No. 210,696, filed Nov. 28, 1980, and now abandoned, which is a continuation-in-part of application Ser. No. 134,389, filed Mar. 27, 1980, and now abandoned.

BACKGROUND OF THE INVENTION

Over the last several years, a variety of approaches to the synthetic or semi-synthetic preparation of insulin have been advanced. Insulin is a molecule having two peptide chains, an A-chain containing 21 amino acid residues and a B-chain containing 30 amino acid residues. These chains contain three disulfide bridges, each formed from two cysteinyl residues. Two of the disulfide bridges join the A-chain to the B-chain. The bridges are formed from the cysteinyl residues at A-6 and A-11, A-7 and B-7, and A-20 and B-19, respectively.

One general method for insulin production is via proinsulin or a proinsulin-like molecule. Proinsulin is a single chain polypeptide in which the N-terminus of the insulin A-chain is linked through a connecting peptide with the C-terminus of the insulin B-chain, the appropriate cysteine residues being joined by disulfide bonds. Human proinsulin, e.g., has 86 amino acid residues, 35 of which make up the connecting peptide. Yanaihara et al., *Diabetes* 27 (Suppl. 1) 149–160 (1978) describe the synthesis of a variety of connecting peptides and human proinsulin.

Other proinsulin-like molecules have been described in the literature, the principal differences from proinsulin being the structure of the moiety which connects the insulin A- and B-chains and the point at which such connection is made.

Thus, Busse et al., *Biochemistry* 15, No. 8, 1649–1657 (1976) report a linkage comprising two methionyl residues joined at their N-terminus by a carbonyl group and the resulting moiety joined to the $N^\alpha$-terminus of the A-1 glycyl and the $N^\epsilon$-terminus of the B-29 lysyl.

Similarly, other connecting moieties have been described. See, for example, Geiger et al., *Biochem. and Biophys. Res. Comm.* 55, 60–66 (1973); Brandenburg et al., *Hoppe-Seyler's Z. Physiol. Chem.* bd. 354, 613–627 (1973); U.S. Pat. Nos. 3,847,893; 3,907,763; 3,883,496; 3,883,500; and 3,884,897.

In any of these approaches for production of insulin via a single chain comprising insulin A- and B-chains joined through a defined moiety, direct interconnection of the insulin A- and B-chains must be carried out by formation of three disulfide bridges from the six cysteinyl residues present on the A- and B-chains. Following disulfide bond formation, the original connecting moiety is removed with formation of insulin.

In effecting this approach to insulin production, an efficient and ready method for correct disulfide bridge formation is highly desirable. In general, the literature methods for forming the disulfide bridges involve air oxidation of the corresponding —SH structures. Furthermore, since it is recognized that the —SH structure is unstable, the precursor normally is generated with an S-protecting group, typically an S-sulfonate (—S—SO$_3^-$) moiety. Thus, the literature methods involve a two-step sequence, i.e., reduction of the S-sulfonate to —SH by treatment with a mercaptan followed by air oxidation of the formed —SH compound.

It now has been discovered that a facile and highly efficient method for direct conversion of the S-sulfonate to the desired disulfide insulin precursor is available. The process does not contemplate a reduction-oxidation sequence. Instead, a direct interchange is effected under conditions that, although not essential, prefer the absence of an oxidizing agent. It is to such a process that this invention is directed.

One possible exception in the prior art to the general two-step method, applied, however, to combination of insulin A- and B-chains and not to disulfide formation from a linear chain S-sulfonate insulin precursor, is represented by Dixon et al., *Nature* 188, 721–724 (1960), which perhaps implies production of insulin by combination of A- and B-chain S-sulfonates in a single solution. The details of this prior art method are quite sketchy, and the yield, based only on activity of the product recovered, represented only 1–2%. A later publication, Dixon, *Proc. Intern. Congr. Endocrinal.* 2nd London 1964, 1207–1215 (1965), appears somewhat to clarify the details of this method, suggesting, in Table IV, page 1211, a two-step process involving anaerobic S-sulfonate reduction followed by oxidation to the disulfide.

SUMMARY OF THE INVENTION

This invention is directed to a process for the production of an insulin precursor of the formula

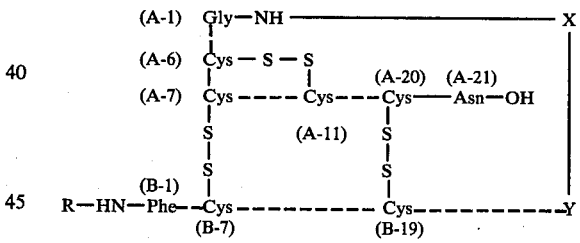

in which R is hydrogen, a chemically or enzymatically cleavable amino acid residue, or a chemically or enzymatically cleavable peptide moiety having at least two amino acid residues; Y is

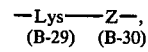

in which Z is

Ala, Thr, or Ser; the moiety from A-1 to A-21 is an insulin A-chain; the moiety from B-1 to B-30 is an insulin B-chain; and X is a moiety which is joined to the insulin A-chain at the amino group of A-1 and to the insulin B-chain at the $\epsilon$-amino group of B-29 or the carboxyl group of B-30, which moiety can be enzymatically or chemically cleaved from and without disruption of both the A-chain and the B-chain, which comprises reacting an S-sulfonate of the formula

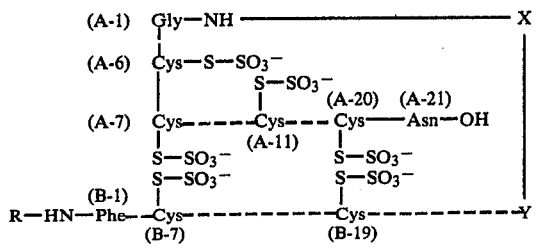

in which R, X, and Y are as aforedefined, with a mercaptan in an amount which provides from about 1 to about 5 —SH moieties per each $—SSO_3^-$ moiety in an aqueous medium at a pH of from about 7 to about 11.5 and at an S-sulfonate concentration of up to about 10 mg. per ml. of aqueous medium.

DETAILED DESCRIPTION OF THE INVENTION

As indicated, this invention is directed to a process for producing an insulin precursor.

As used herein, the term "insulin precursor" refers to a molecule which (1) contains an insulin A-chain and an insulin B-chain, (2) has at least three disulfide bonds represented by a joining of the sulfurs of each of the Cys moieties located in the A- and B-chains at (a) A-6 and A-11, (b) A-7 and B-7, and (c) A-20 and B-19, respectively, and (3) has a removable connecting moiety which is joined to the insulin A-chain at the amino group of A-1 and to the insulin B-chain at the ε-amino group of the lysine residue at B-29 or the carboxyl group of the amino acid residue at B-30.

The group Z, which defines the B-30 amino acid residue of insulin, is any of Ala, Thr, or Ser. These residues represent naturally occurring insulins, Thr in human insulin, Ala in bovine and porcine insulins, and Ser in rabbit insulin.

The group R is hydrogen, and amino acid residue, or a peptide moiety having at least two amino acid residues. In those instances in which R is an amino acid residue or a peptide moiety, R is a group which is cleavable from the insulin precursor product of the process of this invention without loss of the integrity of the residual insulin structure. Any of a wide variety of amino acid residues of peptide moieties qualify within the definition of the group R. Examples of cleavable amino acid residues are basic amino acids such as arginine (Arg) or lysine (Lys) as well as peptide moieties terminating at the carboxyl by such amino acid residues. These are recognized as susceptible to cleavage upon treatment with the proteolytic enzyme trypsin. Another example of a cleavable amino acid residue is methionine (Met) as well, again, as a peptide moiety having Met at its carboxy terminal. These can be removed by treatment with cyanogen bromide. A further example is tryptophan (Trp) or a peptide moiety containing Trp at its carboxy terminal. This is removed upon treatment with N-bromosuccinimide.

The connecting moiety, X, of the insulin precursor and of the linear chain S-sulfonate insulin precursor can be any of a wide range of structures. Preferably, the moiety X is a polypeptide. The polypeptide generally has at least 2 and preferably from about 2 to about 35 and most preferably from about 6 to about 35 amino acid residues. The moiety X is joined to the A-chain at the amino group of A-1 and to the B-chain at the carboxyl group of B-30. Most preferably, the connecting moiety, X, when it is a peptide, is the natural connecting peptide of an insulin precursor, and generally of that insulin represented by one or both of the A- and B-chains to which it is joined. Examples of naturally occurring connecting peptides are the following:

Rabbit: -Arg-Arg-Glu-Val-Glu-Glu-Leu-Gln-Val-Gly-Gln-Ala-Glu-Leu-Gly-Gly-Gly-Pro-Gly-Ala-Gly-Gly-Leu-Gln-Pro-Ser-Ala-Leu-Glu-Ala-Leu-Gln-Lys-Arg-.

Human: -Arg-Arg-Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-Arg-.

Monkey: -Arg-Arg-Glu-Ala-Glu-Asp-Pro-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-Arg-.

Horse: -Arg-Arg-Glu-Ala-Glu-Asp-Pro-Gln-Val-Gly-Glu-Val-Glu-Leu-Gly-Gly-Gly-Pro-Gly-Leu-Gly-Gly-Leu-Gln-Pro-Leu-Ala-Leu-Ala-Gly-Pro-Gln-Gln-Lys-Arg-.

Rat I: -Arg-Arg-Glu-Val-Glu-Asp-Pro-Gln-Val-Pro-Gln-Leu-Glu-Leu-Gly-Gly-Gly-Pro-Glu-Ala-Gly-Asp-Leu-Gln-Thr-Leu-Ala-Leu-Glu-Val-Ala-Arg-Gln-Lys-Arg-.

Rat II: -Arg-Arg-Glu-Val-Glu-Asp-Pro-Gln-Val-Ala-Gln-Leu-Glu-Leu-Gly-Gly-Gly-Pro-Gly-Ala-Gly-Asp-Leu-Gln-Thr-Leu-Ala-Leu-Glu-Val-Ala-Arg-Gln-Lys-Arg-.

Porcine: -Arg-Arg-Glu-Ala-Glu-Asn-Pro-Gln-Ala-Gly-Ala-Val-Glu-Leu-Gly-Gly-Gly-Leu-Gly-Gly-Leu-Gln-Ala-Leu-Ala-Leu-Glu-Gly-Pro-Pro-Gln-Lys-Arg-.

Bovine, Lamb: -Arg-Arg-Glu-Val-Glu-Gly-Pro-Gln-Val-Gly-Ala-Leu-Glu-Leu-Ala-Gly-Gly-Pro-Gly-Ala-Gly-Gly-Leu-Glu-Gly-Pro-Pro-Gln-Lys-Arg-.

Dog: -Arg-Arg-Asp-Val-Glu-Leu-Ala-Gly-Ala-Pro-Gly-Glu-Gly-Gly-Leu-Gln-Pro-Leu-Ala-Leu-Glu-Gly-Ala-Leu-Gin-Lys-Arg-.

Guinea Pig: -Arg-Arg-Glu-Leu-Glu-Asp-Pro-Gln-Val-Glu-Gln-Thr-Glu-Leu-Gly-Met-Gly-Leu-Gly-Ala-Gly-Gly-Leu-Gln-Pro-Leu-Gln-Gly-Ala-Leu-Gln-Lys-Arg-.

Chinchilla: -Arg-Arg-Glu-Leu-Glu-Asp-Pro-Gln-Val-Gly-Gln-Ala-Pro-Gly-Val-Val-Pro-Glu-Ala-Gly-Arg-Leu-Gln-Pro-Leu-Ala-Leu-Glu-Met-Thr-Leu-Gln-Lys-Arg-.

Duck: -Arg-Arg-Asp-Val-Glu-Gln-Pro-Leu-Val-Asn-Gly-Pro-Leu-His-Gly-Glu-Val-Gly-Glu-Leu-Pro-Phe-Gln-His-Glu-Glu-Tyr-Gln-Lys-Arg-.

It is highly preferred that the amino acid sequence represented by A-1 to A-21, X, and B-1 to B-30 is the naturally occurring sequence for the A-chain, the connecting peptide, and the B-chain of porcine, bovine, or human proinsulin, and most preferably, of human proinsulin.

Although it is preferred to use the natural connecting sequence, as indicated above, much shorter peptide sequences can be used for the connecting peptide. The only requirements are (1) that they be of sufficient length to permit proper disulfide bond formation between the A- and B-chains, and (2) that they be cleavable from the insulin precursor with accompanying insulin formation. A typical dipeptide which can be used is -Arg-Arg-. In addition, modifications of the foregoing dipeptide having the formula -Arg-X'-Arg- in which X' represents at least one amino acid residue can be readily employed. Highly preferred connecting peptides are -Arg-Arg-Lys-Arg- as well as longer chain peptides having the structure -Arg-Arg-X$^2$-Lys-Arg- in which X$^2$ is at least one amino acid residue and preferably two amino acid residues. These latter, of course, include the natural connecting peptides, many of which are described above.

Again, subject to the above criteria, any of a wide range of other connecting moieties can be employed. In those instances in which the connecting moiety is a polypeptide, the points of connection are the amino terminal of the A-chain (A-1) and the carboxyl terminal of the B-chain (B-30). However, since the B-29 amino acid residue (Lys) contains an $\epsilon$-amino group, the connecting moiety can be joined to the A- and B-chains via the amino groups at A-1 and B-29. Thus, e.g., carbonylbis(methionyl), described by Busse et al., supra.; 2,2'-sulfonylbis(ethoxycarbonyl), described by Obermeier et al., *Hoppe-Sayler's Z. Physiol. Chem.* 356, 1631-1634 (1975); 2,7-diaminosuberoyl, described by Geiger et al., supra; and the like, represent useful connecting moieties in this latter system.

In carrying out the process of this invention, the linear chain S-sulfonate insulin precursor is treated with a mercaptan in an aqueous medium at a pH of from about 7 to about 11.5. By mercaptan, of course, is meant a compound that contains at least one —SH group. The only limitation upon the mercaptan used in the process of this invention is that it is water soluble.

Examples of typical water soluble mercaptans are dithiothreitol, dithioerythritol, 2-mercaptoethanol, methyl thioglycolate, 3-mercapto-1,2-propanediol, 3-mercaptopropionic acid, and the like. Although mercaptans having multiple —SH groups, such as dithiothreitol, can be used, it is preferred to use a mercaptan having a single —SH group. Of these, 2-mercaptoethanol is highly preferred.

The process of this invention is carried out in an aqueous medium maintained at the desired pH, generally by addition of a suitable buffering agent. The pH of the medium ranges from about 7 to about 11.5. Preferably, however, the pH is from about 9.5 to about 10.5. Any buffering agent, therefore, having buffering capacity within the foregoing broad range can be employed in the process of this invention. Examples of such suitable buffering agents are phosphate buffers, tri(hydroxymethyl)aminomethane (Tris), borate buffers, glycine, and the like.

The concentration of the buffering agent in the aqueous medium generally will range up to about 0.5 N. Preferably, the range will be from about 0.005 N to about 0.5 N, and, more preferably, from about 0.005 N to about 0.1 N.

The linear chain S-sulfonate insulin precursor is incorporated into the aqueous medium at a concentration not greater than about 10 milligrams per milliliter. Preferably, the concentration is lower, generally in the range of from about 0.05 milligrams to about 2 milligrams per milliliter.

An important element of the process of this invention relates to the quantity of mercaptan used relative to the linear chain S-sulfonate insulin precursor. Prior art methods for reducing S-sulfonate to —SH have used very large excesses of mercaptan relative to the S-sulfonate. It is now apparent that such large excesses have overwhelmed the S-sulfonate starting material, producing complete reduction of the S-sulfonate to the corresponding —SH compound. This, in turn, necessitated isolation of the —SH intermediate or high dilution of the reaction mixture followed by a distinct oxidation step, generally using air, to convert the —SH intermediate to the desired —S—S— compound. In this regard, see, for example, Crestfield et al., *J. Biol. Chem.* 238, 622-627 (1963); Steiner et al., *Proc. Nat'l Acad. Sci. U.S.A.* 60, 622-629 (1968); and Yanaihara et al., *Diabetes* 27 (Suppl. 1), 149-160 (1978).

The process of this invention, on the other hand, requires the use of mercaptan in an amount which affords from about 1 to about 5 —SH moieties per each —S—SO$_3$$^-$ moiety, and, preferably, an amount which affords from about 2 to about 4 —SH moieties per —S—SO$_3$$^-$ moiety. When the mercaptan is used in an amount in the range prescribed, it has been discovered that it is possible, with a high degree of efficiency and ease, to convert the linear chain S-sulfonate insulin precursor directly to the desired disulfide insulin precursor. Since the insulin A- and B-chains present as part of the linear chain S-sulfonate insulin precursor contain six S-sulfonate groups, in order to achieve the prescribed range, a mercaptan containing a single —SH group, of course, would be used at a molar ratio of from about 6:1 to about 30:1.

The interrelationship of pH, buffer strength, and concentration of the linear chain S-sulfonate insulin precursor is an important, although not essential, consideration in carrying out the process of this invention. Thus, in general, it is preferred to increase pH and decrease buffer strength with increasing concentration of the linear chain S-sulfonate insulin precursor.

Moreover, in complete distinction from the typical prior art processes, it is not essential to carry out the process of this invention in an oxidizing atmosphere. Although an oxidizing agent, e.g., air, may be present in the reaction medium, it surprisingly has been found to be highly preferred to conduct the reaction in the substantial absence of air or other oxidizing agent. By "substantial absence" is intended only the avoidance of an affirmative addition of air. This is achieved, for example, by carrying out the reaction in a closed system which precludes the availability of air or other oxidizing agent. To further ensure the absence of air, the aqueous medium can be purged with nitrogen and degassed prior to addition of the reactants.

Another highly desirable, although not essential, feature of the process of this invention is temperature control. The process generally is carried out at a temperature of from about 0° C. to about 37° C. Preferably, the reaction temperature is at the lower end of this range, generally from about 2° C. to about 8° C., and, more particularly, from about 4° C. to about 6° C. More preferably, however, the process is carried out at two temperature ranges. The reaction mixture is prepared at about room temperature, and, once so prepared, is cooled to a temperature from about 2° C. to about 8° C. and maintained in the latter range for the remainder of the reaction period.

Typically, therefore, in carrying out the process of this invention, an aqueous medium having the selected pH is prepared using, for example, glycine at about 0.05 N concentration. The thus-prepared aqueous medium, maintained generally at a temperature of from about 0° C. to about 37° C., and, preferably, at about room temperature, is degassed, purged with nitrogen, and again degassed. The linear chain S-sulfonate insulin precursor is dissolved in the aqueous medium in an amount affording the desired concentration, for example, about 0.1 mg./ml. of medium. The mercaptan is added in an amount affording up to about 5 —SH groups per —S—SO$_3^-$ group. The resulting mixture, maintained substantially in the absence of air or other oxidizing agent, is cooled to a temperature of about 4° C. to about 6° C. and is maintained in that range until completion of the reaction. This generally takes from about 5 to about 72 hours, and more generally, from about 15 to about 24 hours, usually about 18 to about 20 hours.

Upon completion of the reaction period, the insulin precursor product can be isolated by any of a wide variety of methods, all of which are well recognized in the field of insulin purification. The most commonly employed methods are chromatographic techniques, including, for example, gel filtration and ion-exchange chromatography.

The resulting insulin precursor can be converted to insulin either enzymatically or chemically, using techniques recognized in the literature. These methods include, for example, cleavage using a combination of trypsin and carboxypeptidase B as described in Kemmler et al., *J. Biol. Chem.* 246, 6786–6791 (1971).

The insulin product can be assayed for purity and relative activity by recognized methods such as polyacrylamide gel electrophoresis, amino acid analysis, radioreceptorassay, radioimmunoassay, high performance liquid chromatography (HPLC), ultraviolet spectrum, dansylation, rabbit blood glucose assay, and the like.

The linear chain S-sulfonate insulin precursor starting materials are available by recombinant DNA methodology. They can also be prepared from natural insulins and proinsulins, as well as by classical peptide synthesis methodology, including either solution or solid-phase techniques.

A linear chain S-sulfonate insulin precursor was prepared from proinsulin as follows: To 100 ml. of chilled deionized 7 M urea were added 786 mg. of sodium sulfite. Solution was complete with stirring. Sodium tetrathionate (594 mg.) then was added. After stirring, most of the sodium tetrathionate had dissolved; however, the solution was cloudy. The pH was adjusted to 7.7 with glacial acetic acid. HPLC purified bovine proinsulin (503 mg.) was added with stirring. The pH of the reaction solution was readjusted to 7.6 with 2 N sodium hydroxide. The resulting slightly cloudy solution was stirred at 6° C. for 18 hours.

Approximately one-half of the reaction mixture was adjusted to pH 9.1 with 2 N sodium hydroxide and applied to a Sephadex G-25 Coarse column. Chromatographic conditions were: solvent, 0.05 M ammonium bicarbonate, pH 9.0; column size, 2×90 cm.; temperature, 21° C.; flow rate, 18.5 ml./minute. The initial 120 ml. of effluent were discarded, and the next 75 ml. were collected and saved. The column then was washed with another 400 ml. of 0.05 M ammonium bicarbonate, pH 9.0. This procedure was repeated for the other half of the reaction solution. UV spectroscopy of the two pools indicated a total of 401 mg. recovered. These pools were combined and lyophilized to dryness. A total of 445.7 mg. of the dry desalted product was collected. The product, linear chain S-sulfonated bovine proinsulin, and an absence of starting material, were confirmed by cellulose acetate electrophoresis and polyacrylamide disc-gel electrophoresis.

The linear chain S-sulfonated beef proinsulin was purified by DEAE cellulose chromatography. The crude sample (443 mg.) was dissolved in 10 ml. of 7.5 M urea-0.01 M Tris-0.001 M EDTA, pH 8.5, and applied to a DEAE cellulose column. Chromatographic conditions were: solvent, 7.5 M urea-0.01 M Tris-0.001 M EDTA, pH 8.5, with a gradient of 0—0.35 M sodium chloride; column size, 2.5×90 cm.; temperature, 4° C.; flow rate, about 0.9 ml./minute; fraction volume, 5.3 ml.

Absorbance at 276 nm. of each fraction plotted versus fraction number indicated a large peak which tailed somewhat. UV spectroscopy indicated the large peak was product. Fractions 199–240 having effluent volumes 1069–1291 ml. were combined. UV spectroscopy indicated 355 mg. in this sample.

The product pool was desalted on a Sephadex G-25 Coarse column. Chromatographic conditions were: solvent, 0.05 M ammonium bicarbonate, pH 8.0; column size, 3.7×105 cm.; temperature, 4° C.; flow rate, 16.0 ml./minute. The initial 395 ml. of effluent were discarded, and the next 250 ml. were collected and saved. The column then was washed with another 2000 ml. of 0.05 M ammonium bicarbonate, pH 8.0. UV spectroscopy of the pool indicated 321 mg. in this sample. The sample was lyophilized to dryness. A total of 373 mg. of the dry material was collected. The identity of the product was verified by polyacrylamide disc gel electrophoresis and by high performance low pressure liquid chromatography on the basis of elution position.

As illustrative of the process of this invention, the following examples are provided. These examples are not intended to be limiting upon the scope of this invention.

EXAMPLE I

Using 0.1 mg./ml. concentration

A solution of 1.61 mg. of linear chain S-sulfonate bovine proinsulin dissolved in 16.1 ml. of degassed 0.05 M glycine, pH 9.5, was prepared. To this solution was added 0.158 ml. of an aqueous 2-mercaptoethanol stock solution which, by titration with Ellman's reagent, was shown to have a mercaptan concentration of 2.11 mg./ml. This represents 4 equivalents of 2-mercaptoethanol per —SSO$_3^-$ in the linear chain S-sulfonate bovine proinsulin. The final pH was 9.46. The solution, prepared at room temperature, was sealed with parafilm and then was stirred with cooling at 6° C. for 19 hours.

The reaction mixture then was acidified to pH 4.0±0.1 (temperature adjusted) using concentrated hydrochloric acid and 0.5 N sodium hydroxide. The product was isolated and verified using high performance low pressure liquid chromatography (HPLPLC). HPLPLC conditions were: column, 1.1×54 cm. glass column packed with LP-1/C$_{18}$ 16.6% C content; solvent, 30% acetonitrile/70% (0.1 M ammonium formate, pH 4.25); temperature, 21° C.; pressure, 114 psi; flow rate, 2.40 ml./minute. Samples were applied to the column by a 5 ml. sample-loop injector and were monitored at 280 nm.

The first sample applied was 5 ml. of a bovine proinsulin stock solution which had a 0.1 mg./ml. nominal protein concentration. The second sample applied was 5 ml. of the acidified reaction mixture. The presence of monomeric bovine proinsulin in the reaction mixture was verified on the basis of elution position. Calculation of areas of the peaks of the two HPLPLC runs indicated an 82.6% yield of bovine proinsulin in the reaction mixture.

EXAMPLE II

Using 0.5 mg./ml. concentration

A solution of 25.07 mg. of linear chain S-sulfonate bovine proinsulin dissolved in 50.14 ml. of degassed 0.05 M glycine, pH 10.51, was prepared. To the solution were added 1.302 ml. of an aqueous 2-mercaptoethanol stock solution which, by titration with Ellman's reagent, was shown to have a mercaptan concentration of 2.10 mg./ml. This represents 2.1 equivalents of 2-mercaptoethanol per $-SSO_3^-$ in the linear chain S-sulfonate bovine proinsulin. The final pH was 10.47. The solution, prepared at room temperature, was sealed with parafilm and then was stirred with cooling at 6° C. for 18 hours.

The reaction mixture then was acidified to pH 4.0±0.1 (temperature adjusted) using concentrated hydrochloric acid and 0.1 N hydrochloric acid. Analysis by HPLPLC indicated a 69% yield of bovine proinsulin in the reaction mixture.

The product, after desalting, was isolated using gel filtration chromatography. The reaction mixture was adjusted to pH 9.0 with concentrated ammonium hydroxide and applied to a Sephadex G-25 Course column. Desalting chromatographic conditions were: solvent, 0.05 M ammonium bicarbonate, pH 9.0; column size, 2×90 cm.; temperature, 21° C.; flow rate, 18.5 ml./minute. The initial 120 ml. of effluent were discarded, and the next 75 ml. were collected and saved (protein pool). The column then was washed with another 400 ml. of 0.05 M ammonium bicarbonate, pH 9.0. UV spectroscopy of the protein pool indicated 21.6 mg. of protein recovered. The pool was lyophilized to dryness. A total of 22.21 mg. of the dry, desalted protein was collected.

A portion of this material (14.84 mg.) was dissolved in 5.5 ml. of 1.0 M acetic acid. UV spectroscopy of the clear solution indicated a 2.56 mg./ml. protein concentration. Five ml. of this solution (12.8 mg. by UV) were applied to a Sephadex G-50 Superfine column. Chromatographic conditions were: solvent, 1 M acetic acid; column size, 1.5×100 cm.; temperature, 21° C.; flow rate, 0.19 ml./minute; fraction volume, about 1.9 ml.

Absorbance at 280 nm. was monitored as the column was eluted overnight with 1 M acetic acid. The resulting graph indicated two peaks. The first, smaller peak represented the aggregated forms of bovine proinsulin. The second peak was monomeric bovine proinsulin. Pools were collected of the two peaks. Fractions combined and their effluent volumes were:

Pool I: Fractions 30–46 (55.0–84.0 ml.; peak, 70.4 ml.)
Pool II: Fractions 47–62 (84.0–112.0 ml.; peak, 99.8 ml.)

UV spectroscopy indicated 1.94 mg. in Pool I and 10.11 mg. in Pool II. This totaled 12.05 mg. and represented a 94.1% recovery of the amount applied to the column. Of the total recovered, 83.9% was monomeric bovine proinsulin.

Both pools were lyophilized to dryness. The product in Pool II was verified as bovine proinsulin on the basis of elution position in a HPLPLC run. It was also verified by treatment with trypsin and carboxypeptidase B using the literature procedure to produce bovine insulin.

EXAMPLE III

Effect of Temperature

The procedure of Example I was used to determine the effect of temperature on the yield of bovine proinsulin from linear chain S-sulfonate bovine proinsulin. The reaction conditions were: protein concentration, 0.1 mg./ml.; buffer, 0.05 M glycine; pH, 9.5; mercaptan, 2-mercaptoethanol in an amount providing 4 equivalents of $-SH$ per $-SSO_3^-$; time, 18 hours.

When the reaction was carried out at 21° C., the yield of proinsulin determined by HPLPLC was 47%. When the reactants were mixed at 21° C. and the temperature of the mixture lowered to 6° C., the yield was 77%.

EXAMPLE IV

Effect of pH

The procedure of Example I was used to determine the effect of pH on the yield of bovine proinsulin from linear chain S-sulfonate bovine proinsulin in a series of reactions carried out simultaneously. The reaction conditions were: protein concentration, 0.5 mg./ml.; buffer, 0.05 M glycine; mercaptan, 2-mercaptoethanol in an amount providing 2 equivalents of $-SH$ per $-SSO_3^-$; time, 18 hours; temperature, 6° C.

The following yields of proinsulin, determined by HPLPLC, were obtained:

| pH | Yield, % |
|---|---|
| 9.0 | 43.1 |
| 9.5 | 44.3 |
| 10.0 | 66.7 |
| 10.5 | 76.0 |
| 11.0 | 61.0 |

EXAMPLE V

Effect of Protein Concentration

The procedure of Example I was used to determine the effect of protein concentration on the yield of bovine proinsulin from linear chain S-sulfonate bovine proinsulin in a series of reactions carried out simultaneously. The reaction conditions were: buffer, 0.05 M glycine; pH, 9.5; mercaptan, 2-mercaptoethanol in an amount providing 4 equivalents of $-SH$ per $-SSO_3^-$; time, 18 hours; temperature, 6° C.

The following yields of proinsulin, determined by HPLPLC, were obtained:

| Protein Concentration, mg./ml. | Yield, % |
|---|---|
| 0.1 | 78 |
| 0.2 | 63 |
| 0.3 | 46 |
| 0.4 | 37.6 |
| 0.5 | 25.4 |
| 1.0 | 12 |

Another series was run at 2 equivalents of $-SH$ per $-SSO_3^-$ and pH 10.5 with the following results:

| Protein Concentration, mg./ml. | Yield, % |
|---|---|
| 0.5 | 77.2 |
| 0.96 | 58.3 |
| 1.83 | 19.5 |
| 4.2* | 20.1 |

| Protein Concentration, mg./ml. | Yield, % |
|---|---|
| 7.4* | 19.6 |

*—SH:—SSO$_3^-$ ratio = 1.2.

EXAMPLE VI

Effect of —SH: —SSO$_3^-$ Ratio

The procedure of Example I was used to determine the effect of the ratio of —SH to —SSO$_3^-$ on the yield of bovine proinsulin from linear chain S-sulfonate bovine proinsulin in a series of reactions carried out simultaneously. The reaction conditions were: protein concentration, 0.5 mg./ml.; buffer, 0.05 M glycine; pH, 9.5., time, 18 hours; temperature, 6° C.

The following yields of proinsulin, determined by HPLPLC, were obtained:

| Ratio, —SH:—SSO$_3^-$ | Yield, % |
|---|---|
| 4.0 | 30.8 |
| 2.0 | 44.7 |
| 1.0 | 37.0 |
| 0.5 | 4.5 |

EXAMPLE VII

Effect of Type of mercaptan

The procedure of Example I was used to determine the effect of mercaptan structure on the yield of bovine proinsulin from linear chain S-sulfonate bovine proinsulin in a series of reactions carried out simultaneously. The reaction conditions were: protein concentration, 0.1 mg./ml.; buffer, 0.05 M glycine; pH, 9.5; mercaptan, 4 equivalents —SH per —SSO$_3^-$; time, 18 hours; temperature, 6° C.

The following yields of proinsulin, determined by HPLPLC, were obtained:

| Mercaptan | Yield, % |
|---|---|
| Dithiothreitol | 39.3 |
| Dithioerythritol | 34.9 |
| Methyl thioglycolate | 56.1 |
| 3-Mercapto-1,2-propanediol | 65.5 |
| 3-Mercaptopropionic acid | 65.3 |
| 2-Mercaptoethanol | 64.1 |

EXAMPLE VII

Effect of Type of Protein

The procedure of Example I was used to determine the effect of protein type on the yield of proinsulin from linear chain S-sulfonate proinsulin in a series of reactions carried out simultaneously. The reaction conditions were: protein concentration, 0.1 mg./ml.; buffer, 0.05 M glycine; pH, 9.5; mercaptan, 2-mercaptoethanol in an amount providing 4 equivalents of —SH per —SSO$_3^-$; time, 18 hours; temperature, 6° C.

The following yields of proinsulin, determined by HPLPLC, were obtained:

| Linear Chain S—sulfonate Proinsulin | Yield, % |
|---|---|
| Bovine | 60.6 |
| Porcine | 65.8 |

EXAMPLE IX

Production of Human Proinsulin

A solution of 169.3 mg. of biosynthetically-produced linear chain S-sulfonate human proinsulin dissolved in 338.6 ml. of degassed 0.05 M Glycine, pH=10.54 was prepared. To this solution were added 7.71 ml. of an aqueous 2-mercaptoethanol stock solution which, by titration with Ellman's reagent, was shown to have a mercaptan concentration of 2.08 mg./ml. This represents 2 equivalents of 2-mercaptoethanol per —SSO$_3^-$ in the linear chain S-sulfonate human proinsulin. The final pH of 10.52 was achieved by a slight adjustment using 5 N sodium hydroxide. This solution was sealed with parafilm and was stirred at 6° C. for 18 hours.

The reaction mixture then was acidified to pH 2.9±0.1 (temperature adjusted) using concentrated hydrochloric acid. The resulting clear solution was applied to a Sephadex G-25 Coarse desalting column. Chromatographic conditions: solvent, 2% acetic acid (v/v); column size, 5×100 cm.; temperature, 25° C.; flow rate, 28.8 ml./minute; fraction volume, 20.2 ml.

The initial 779 ml. of effluent were discarded, and the next 464 ml. were collected and saved. On the basis of optical density monitoring at 280 nm., this was determined to be the protein pool. The column was washed with an additional 2500 ml. of 2% acetic acid. Calculations based on the UV spectrum of the protein pool indicated a recovery of 164 mg. of protein, which represented 101.9% of the amount applied to the column (the theoretical yield of the reformation reaction). This pool was frozen and lyophilized to dryness.

The desired product was isolated using gel filtration chromatography. The dry material (unweighed) was dissolved in 20 ml. of 1 M acetic acid. The resulting clear solution was applied to a Sephadex G-50 Superfine column. Chromatographic conditions: solvent, 1 M acetic acid; column size, 2.5×125 cm.; temperature, 25° C.; flow rate, ~0.82 ml./minute; fraction volume, ~4.92 ml.

Absorbance at 280 nm. was monitored as the column was eluted with 1 M acetic acid overnight. The resulting graph of absorbance at 280 nm. versus fraction number indicated 2 main peaks. The first peak (smaller) represented the aggregated forms of human proinsulin. The second peak was good monomeric human proinsulin. It also had a front side shoulder. Three pools of fractions were collected. Fractions combined and their effluent volumes were:

Pool I: fractions 46-67 (218-325.5 ml.)
Pool II: fractions 68-81 (325.5-395.5 ml.)
Pool III: fractions 82-100 (395.5-490.3 ml.)

The following amounts of protein were calculated from the UV spectra of these pools:

Pool I: 22.1 mg.
Pool II: 28.3 mg.
Pool III: 103.6 mg.

This totaled 154 mg. and represented a 94% recovery of the amount applied to the column. Of the amount recovered, 67.3% was monomeric human proinsulin. All 3 pools were frozen and lyophilized to dryness.

A total of 106.55 mg. of dry material was collected from pool III. It was verified as human proinsulin by amino acid analysis and polyacrylamide disc gel electrophoresis. It also eluted on HPLC in a position where human proinsulin would be expected to elute relative to bovine proinsulin. It was further verified by treatment with trypsin and carboxypeptidase B to produce human insulin.

I claim:

1. A process for the production of an insulin precursor of the formula

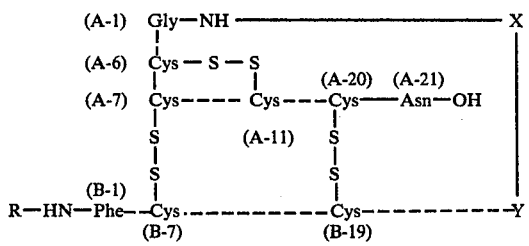

in which R is hydrogen, a chemically or enzymatically cleavable amino acid residue, or a chemically or enzymatically cleavable peptide moiety having at least two amino acid residues, Y is

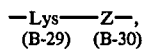

in which Z is Ala, Thr, or Ser; the moiety from A-1 to A-21 is an insulin A-chain; the moiety from B-1 to B-30 is an insulin B-chain; and X is a moiety which is joined to the insulin A-chain at the amino group of A-1 and to the insulin B-chain at the ε-amino group of B-29 or the carboxyl group of B-30, which moiety can be enzymatically or chemically cleaved from and without disruption of both the A-chain and the B-chain, which comprises reacting an S-sulfonate of the formula

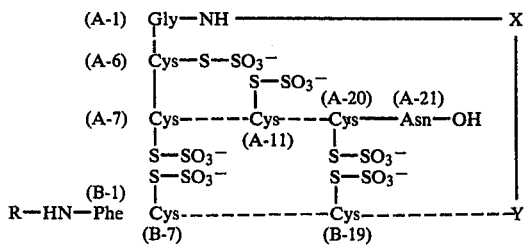

in which R, X, and Y are as aforedefined, with a mercaptan in an amount which provides from about 1 to about 5 —SH moieties per each —SSO$_3^-$ moiety in an aqueous medium at a pH of from about 7 to about 11.5 and at an S-sulfonate concentration of up to about 10 mg. per ml. of aqueous medium.

2. Process of claim 1, in which R is hydrogen.

3. Process of claim 2, in which X is a peptide moiety joined to the insulin B-chain at the carboxyl group of B-30.

4. Process of claim 3, in which X is -Arg-X'-Arg- in which X' is at least one amino acid residue.

5. Process of claim 4, in which X is -Arg-Arg-X$^2$-Lys-Arg- in which X$^2$ is at least one amino acid residue.

6. Process of claim 5, in which the reaction is carried out at a pH of from about 9.5 to about 10.5.

7. Process of claim 6, in which the mercaptan is present in an amount which provides from about 2 to about 4 —SH moieties per —SSO$_3^-$ moiety.

8. Process of claim 7, in which the reaction is carried out in the substantial absence of an oxidizing agent.

9. Process of claim 8, in which the concentration of S-sulfonate is from about 0.05 milligrams to about 2 milligrams per milliliter of aqueous medium.

10. Process of claim 9, in which the mercaptan is 2-mercaptoethanol.

11. Process of claim 10, in which the reaction is carried out at a temperature of from about 2° C. to about 8° C.

12. Process of claim 11, in which the reaction is carried out at a temperature of from about 4° C. to about 6° C.

13. Process of claim 12, in which the reaction mixture is prepared at about room temperature, and the reaction is allowed to proceed with cooling to a temperature within the range of from about 4° C. to about 6° C.

14. Process of claim 13, in which the pH of the reaction mixture is maintained by addition of a buffering agent at a concentration of from about 0.01 N to about 0.5 N.

15. Process of claim 14, in which the buffering agent is glycine.

16. Process of claim 15, in which the insulin A-chain and the insulin B-chain of the S-sulfonate have the structure of human insulin.

17. Process of claim 16, in which X is the connecting peptide of human insulin.

* * * * *